United States Patent [19]

Charles et al.

[11] Patent Number: 4,567,034
[45] Date of Patent: Jan. 28, 1986

[54] ESTERS OF DIATRIZOIC ACID AS X-RAY CONTRAST AGENTS

[75] Inventors: Isabel Charles, Wirral; Malcolm Robinson, South Wirral, both of United Kingdom

[73] Assignee: E. R. Squibb & Sons, Inc., Princeton, N.J.

[21] Appl. No.: 648,393

[22] Filed: Sep. 7, 1984

[51] Int. Cl.$^4$ .................. A61K 49/04; C07C 101/68
[52] U.S. Cl. ........................................... 424/5; 560/47
[58] Field of Search ............................. 560/47; 424/5

[56] References Cited

U.S. PATENT DOCUMENTS

| | | | |
|---|---|---|---|
| 3,097,228 | 7/1963 | Larsen | 560/47 |
| 3,128,301 | 4/1964 | Larsen et al. | 424/5 |
| 3,476,802 | 11/1969 | Holtermann et al. | 560/47 |
| 3,637,824 | 1/1972 | Holtermann et al. | 560/47 |
| 3,772,376 | 11/1973 | Ekstrand et al. | 560/47 |
| 3,795,698 | 3/1974 | Soulal et al. | 560/47 |
| 4,018,783 | 4/1977 | Soulal et al. | 560/47 |
| 4,132,731 | 1/1979 | Klieger et al. | 424/5 |
| 4,192,859 | 3/1980 | Mackaness et al. | 424/5 |
| 4,225,725 | 9/1980 | Hoey | 560/47 |
| 4,285,928 | 8/1981 | Wada et al. | 424/5 |

FOREIGN PATENT DOCUMENTS

| | | | |
|---|---|---|---|
| 3001292 | 7/1981 | Fed. Rep. of Germany | 560/47 |
| 779500 | 7/1957 | United Kingdom | 560/47 |
| 866184 | 4/1961 | United Kingdom | 560/47 |
| 2041221 | 9/1980 | United Kingdom | 424/5 |

OTHER PUBLICATIONS

Havron et al., "Radiopaque Liposomes: A Promising New Contrast Material for Computed Tomography of the Spleen", Radiology, 140:507–511, Aug. 1981.

Ryan et al., "The Preparation and Characterization of Liposomes Containing X-Ray Contrast Agents", Biochemica et Biophysica Acta. 756 (1983), 106–110 (Elsevier Biomedical Press).

Primary Examiner—Natalie Trousof
Assistant Examiner—Bruce D. Gray
Attorney, Agent, or Firm—Lawrence S. Levinson; Burton Rodney

[57] ABSTRACT

New X-ray contrast agents are provided which are esters of diatrizoic acid having the structure

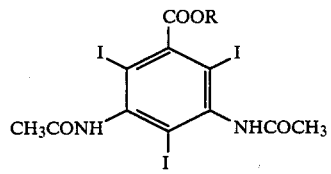

wherein R is an alkyl group of 10 to 22 carbons or a group of the structure

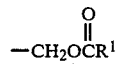

wherein R$^1$ is an alkyl group of 2 to 15 carbons. X-ray contrast medium containing the above X-ray contrast agent and a carrier therefor such as a liposome carrier, and a method for the X-ray visualization of body cavities and organs are also provided.

14 Claims, No Drawings

ESTERS OF DIATRIZOIC ACID AS X-RAY CONTRAST AGENTS

FIELD OF THE INVENTION

The present invention relates to esters of diatrizoic acid which are useful as contrast agents, to X-ray contrast media containing such contrast agents, which may include a liposome carrier, and to a method of using the above X-ray contrast media in the X-ray visualization of body cavities and organs.

BACKGROUND OF THE INVENTION

The use of certain iodine-containing benzoic acid derivatives as X-ray contrast agents is well known. For example, U.S. Pat. No. 4,018,783 to Soulal discloses X-ray contrast agents which are of the structure

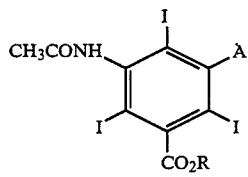

wherein A is —CONHCH$_3$ or —N(CH$_3$)COCH$_3$ and R is a phthalide group or lower alkyl optionally substituted with an aryl or dialkylamino group, or with a group of the formula

—OCOR$_1$ wherein R$_1$ is lower alkyl, except that when A is —CONHCH$_3$, then R is not acetoxymethyl or pivaloyloxymethyl.

British Pat. No. 866,184 discloses triiodobenzoic acid derivatives of the structure

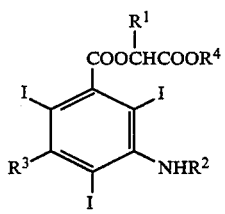

wherein R$^1$ is H or lower alkyl; R$^2$ is H or lower alkanoyl; R$^3$ is H or lower alkanoylamino.

U.S. Pat. No. 3,128,301 discloses 3,5-diacylamino-2,4,6-triiodobenzoic acid esters of the structure

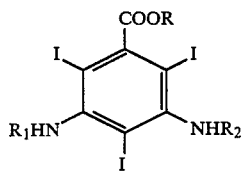

wherein R is lower alkyl, and R$_1$ and R$_2$ are lower alkanoyl.

U.S. Pat. No. 4,192,859 to Mackaness et al discloses the use of liposomes as carriers for contrast agents such as diatrizoic acid, sodium diatrizoate and other iodinated contrast agents.

Havron et al in "Radiopaque Liposomes: A Promising New Contrast Material for Computed Tomography of the Spleen", Radiology 140:507-511, August, 1981, disclose radiopaque positively charged liposomes as carriers for diatrizoate meglumine and diatrizoate sodium (Renografin) for use in computed tomography of the spleen.

Ryan et al in "The Preparation and Characterization of Liposomes Containing X-Ray Contrast Agents," Biochemica et Biophysica Acta. 756 (1983), 106–110 (Elsevier Biomedical Press) disclose use of Renografin and Hypaque in liposomes in X-ray computed tomography.

DESCRIPTION OF THE INVENTION

In accordance with the present invention, new X-ray contrast agents are provided having the formula I

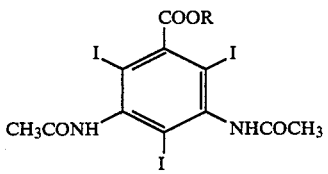

wherein R is an alkyl contains 10 to 22 carbons, and preferably 14 to 20 carbons, or a group of the structure

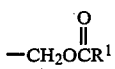

—CH$_2$OCR$^1$ wherein R$^1$ is an alkyl group of 2 to 15 carbons, and preferably 4 to 12 carbons.

Thus, the compounds of formula I of the invention cover compounds of the following structures

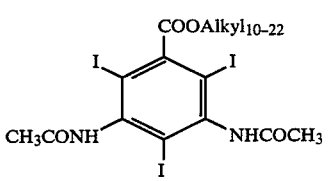

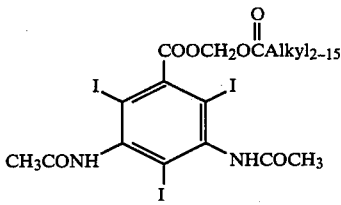

Further in accordance with the present invention, there is provided an X-ray contrast media composition which includes a compound of formula I together with a suitable pharmaceutically acceptable carrier therefor.

The term "alkyl" as employed herein includes both straight and branched chain radicals of 10 to 22 carbons, preferably 14 to 20 carbons in the case of R, and 2 to 15 carbons, preferably 4 to 12 carbons, in the case of R$^1$. Examples of suitable R and R$^1$ alkyl groups include, but are not limited to decyl, undecyl, dodecyl, tridecyl, tetradecyl, pentadecyl, hexadecyl, septadecyl, octadecyl, nonadecyl, eicosanyl, heneicosanyl, and docosanyl, and including the various branched chain-isomers thereof.

The esters of diatrizoic acid of the invention may be prepared by using conventional esterification techniques. For example, in preparing the long chain esters of formula IA, diatrizoic acid of structure A

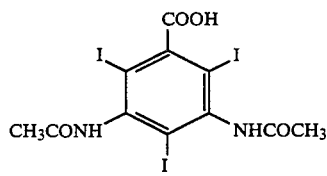

A is reacted with an appropriate alcohol of structure B

ROH.  B

In a preferred process, diatrizoic acid is reacted with an alkali metal hydroxide such as KOH or NaOH to form the corresponding alkali metal diatrizoate which in turn, is reacted with an alkyl halide of the structure C

RX  C wherein X is Br, Cl or I, in the presence of an inert organic solvent such as acetone, dimethyl formamide and an alkali metal iodide such as KI.

Compounds of formula IB may be prepared by reacting diatrizoic acid with an aqueous alkali metal hydroxide such as KOH or NaOH to form the corresponding salt. A solution of the diatrizoate salt in water is then treated with a tetraalkylammonium halide, for example, benzyltributylammonium chloride, in the presence of a water immiscible organic solvent, such as chloroform, dichloromethane or toluene. A halomethyl ester of the structure D is added

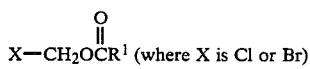

D and the mixture is allowed to react for 1 to 16 days to form IB.

The X-ray contrast medium of the invention which includes an X-ray contrast agent of the invention and a pharmaceutically acceptable carrier therefor, may be used in X-raying and scanning body cavities and organs.

In a more preferred embodiment of the invention, the X-ray contrast agent of formula I is incorporated in a liposome carrier employing procedures as described in U.S. Pat. No. 4,192,859 and as such is especially useful in lymphographic techniques.

The X-ray contrast agent of the invention will be present in the liposome contrast medium in an amount within the range of from about 20 to about 60% by weight of the contrast medium, and preferably from about 30 to about 50% by weight of the contrast medium, depending upon the desired concentration of iodine.

The liposomes and preparations for same suitable for use herein include those disclosed in U.S. Pat. No. 3,957,971 to Oleniacz; G. Sessa et al, J. Lipid Res., Vol. 9, 310 (1968), as well as in the various references discussed hereinbefore, and other liposomes known in the art.

Liposomes employed in the present invention generally comprise lipid materials, predominantly of the phospholipid type (for example, a sterol), lecithin, dicetyl phosphate, or stearylamine, in an organic solvent.

When employing an X-ray contrast medium containing an X-ray contrast agent and a liposome carrier therefor, according to the invention, the X-ray contrast medium is administered to the body of the test object whereafter the body is exposed to X-rays and photographs may be taken or the image observed directly on a fluorescent screen, or other X-ray techniques may be applied in a conventional manner. The dose of contrast medium administered is selected according to the category of the investigation, so that a sufficient contrast effect is obtained.

The test object may include mammalian species, such as humans, dogs, cats, monkeys, sheep, pigs, horses, bovine animals and the like.

As indicated, the X-ray contrast medium of the invention is particularly suitable for use in lymphography. However, the X-ray contrast medium may be employed for visualizing many different body cavities and organs, such as the chest cavity including the bronchial tree, and the gastrointestinal tract. In the latter instance, the contrast medium is administered perorally as a thick liposomal formulation. The intestines can also be visualized by administering the X-ray contrast medium rectally in the form of a liposomal enema. Another example is the visualization of blood vessels subsequent to the X-ray contrast medium being injected in the form of a sterile liposomal preparation. When injected intraveneously the X-ray contrast medium is excreted with the urine and enables visibilization of the renal pelvis, ureters and bladders. Further examples are the use of the X-ray contrast media in imaging the biliary system, hysterosalpingography, cholangiography, myelography, angiography, sialography, and liver and spleen imaging.

As indicated, the X-ray contrast agent of the invention may be combined with a pharmaceutically acceptable carrier (other than liposomes) depending upon the particular use of the final composition which may be employed for diagnostic purposes in bronchography, the delineation of tissue planes, salpinography and transumbilical heptography. In such applications, the X-ray contrast agents of the invention may be administered as an aqueous dispersion, an aerosol, in microencapsulated form or in an oily solution. Thus, for bronchography, the X-ray contrast agent of the invention may be combined with a non-toxic water-insoluble or metabolizable solid carrier, such as lactose, for purpose of insufflation.

The following Examples represent preferred embodiments of the present invention.

EXAMPLE 1

Octadecyl Diatrizoate

A solution of potassium hydroxide (5.36 g of 85% purity) in water (17 ml) was added to diatrizoic acid (50 g), followed by acetone (300 ml), 1-bromooctadecane (30 g) and potassium iodide (5 g). The suspension was stirred and heated at 56° C. (under reflux) for 10 days. The insoluble material was collected by filtration and washed with ethyl acetate. The solid was then extracted with hot (60° C.) methanol-chloroform (1:1) and the solution obtained was filtered and concentrated to give octadecyl diatrizoate, which was recrystallized from 1:1 methanol:chloroform. The white solid had a m.p. 248°–250° C.(d).

EXAMPLE 2

Pivaloyloxymethyl Diatrizoate

Aqueous N sodium hydroxide (33 ml) was added to a stirred suspension of diatrizoic acid (20 g) in water (20 ml), followed by benzyltributylammonium chloride (10.2 g), chloroform (55 ml) and chloromethyl pivalate (5 ml). The reaction mixture was stirred vigorously at room temperature for 2 weeks. The precipitated solid was collected by filtration and recrystallized from methanol-chloroform, affording the pivaloyloxymethyl diatrizoate as white crystals, m.p. 253°–254.5° C.(d).

EXAMPLE 3

Nonadecyl Diatrizoate

Following the procedure of Example 1 except substituting 1-bromononadecane for 1-bromooctadecane, the title compound is obtained.

EXAMPLE 4

Septadecyl Diatrizoate

Following the procedure of Example 1 except substituting 1-bromoseptadecane for 1-bromooctadecane, the title compound is obtained.

EXAMPLE 5

Pentadecyl Diatrizoate

Following the procedure of Example 1 except substituting 1-bromopentadecane for 1-bromooctadecane, the title compound is obtained.

EXAMPLE 6

Dodecyl Diatrizoate

Following the procedure of Example 1 except substituting 1-bromododecane for 1-bromooctadecane, the title compound is obtained.

EXAMPLE 7

Eicosanyl Diatrizoate

Following the procedure of Example 1 except substituting 1-bromoeicosane for 1-bromooctadecane, the title compound is obtained.

EXAMPLE 8

Docosanyl Diatrizoate

Following the procedure of Example 1 except substituting 1-bromodocosane for 1-bromooctadecane, the title compound is obtained.

EXAMPLE 9

Hexanoyloxymethyl Diatrizoate

Following the procedure of Example 2 except substituting chloromethyl hexanoate for chloromethyl pivalate, the title compound is obtained.

EXAMPLE 10

Valeroyloxymethyl Diatrizoate

Following the procedure of Example 2 except substituting chloromethyl valerate for chloromethyl pivalate, the title compound is obtained.

EXAMPLE 11

Octanoyloxymethyl Diatrizoate

Following the procedure of Example 2 except substituting chloromethyl octanoate for chloromethyl pivalate, the title compound is obtained.

EXAMPLE 12

Decanoyloxymethyl Diatrizoate

Following the procedure of Example 2 except substituting chloromethyl decanoate for chloromethyl pivalate, the title compound is obtained.

EXAMPLE 13

Propanoyloxymethyl Diatrizoate

Following the procedure of Example 2 except substituting chloromethyl propanoate for chloromethyl pivalate, the title compound is obtained.

EXAMPLE 14

Pentadecanoyloxymethyl Diatrizoate

Following the procedure of Example 2 except substituting chloromethyl pentadecanoate for chloromethyl pivalate, the title compound is obtained.

EXAMPLE 15

A quantity of each of 1.4 g egg lecithin (egg phosphotidyl choline) and 0.6 g cholesterol are dissolved in 20 ml of chloroform. The chloroform is evaporated leaving a film of neutral phospholipid residue. Two grams of the phospholipid is then added to 7 ml of neutral buffered solution containing 4 g of the X-ray contrast agent octadecyl diatrizoate prepared as described in Example 1. The mixture is stirred with a magnetic stirrer until a final homogeneous liposomal mixture is obtained. Ten milliliters of the final liposome preparation contains 4 g of the X-ray contrast agent.

The so-formed X-ray contrast medium may be employed as described in U.S. Pat. No. 4,192,859.

EXAMPLE 16

Two grams of neutral phospholipid residue, prepared as described in Example 15, is added to 6.7 ml of neutral buffered solution containing 4 g of pivaloyloxymethyl diatrizoate. The mixture is stirred with a magnetic stirrer until a homogeneous liposomal mixture is obtained. Ten milliliters of the final liposome preparation contains 4 g of pivaloyloxymethyl diatrizoate.

The so-formed contrast medium may be employed as described in U.S. Pat. No. 4,182,859.

EXAMPLE 17

An X-ray contrast composition is prepared by admixing octadecyl diatrizoate acid (10 g) and lactose (0.5 g).

EXAMPLE 18

An X-ray contrast composition is prepared by admixing pivaloyloxymethyl diatrizoate (10 g) and lactose (0.5 g).

What is claimed is:

1. An X-ray contrast agent having the structure

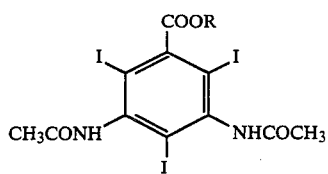

wherein R is an alkyl group of from 10 to 22 carbons.

2. The compound as defined in claim 2 wherein R is an alkyl group of 14 to 20 carbons.

3. The compound as defined in claim 1 wherein R is an alkyl group of 14 to 20 carbons.

4. An X-ray contrast medium comprising an X-ray contrast agent as defined in claim 1 and a carrier therefor.

5. The X-ray contrast medium as defined in claim 4 wherein said carrier is a liposome.

6. The X-ray contrast medium as defined in claim 4 wherein said contrast agent is octadecyl diatrizoate.

7. A method for the X-ray visualization of body cavities and organs, which comprises administering to the body of the test object an effective contrast producing amount of an X-ray contrast medium as defined in claim 4.

8. The method as defined in claim 4 wherein the liver is visualized.

9. The method as defined in claim 4 wherein the spleen is visualized.

10. The method as defined in claim 4 wherein the gall bladder is visualized.

11. The method as defined in claim 4 wherein the spinal cord is visualized.

12. The method as defined in claim 4 wherein the X-ray contrast agent employed is the octadecyl diatrizoate.

13. The method for X-ray visualization of lymphatic channels, which comprises administering to the body of the test object an effective contrast producing amount of an X-ray contrast medium as defined in claim 5.

14. A method for the radiographic examination of the gastrointestinal tract, which comprises administering to the body of the test object an effective contrast producing amount of an X-ray contrast medium as defined in claim 4.

* * * * *